US012350087B2

(12) United States Patent
Bindley et al.

(10) Patent No.: US 12,350,087 B2
(45) Date of Patent: Jul. 8, 2025

(54) SYSTEMS AND METHODS FOR MEASURING BONE MASS DENSITY USING ENERGY DISCRIMINATING PHOTON-COUNTING X-RAY DETECTOR

(71) Applicant: REDLEN TECHNOLOGIES, INC., Saanichton (CA)

(72) Inventors: Glenn Bindley, Victoria (CA); Krzysztof Iniewski, Port Moody (CA)

(73) Assignee: REDLEN TECHNOLOGIES, INC., Saanichton (CA)

( * ) Notice: Subject to any disclaimer, the term of this patent is extended or adjusted under 35 U.S.C. 154(b) by 330 days.

(21) Appl. No.: 18/177,460

(22) Filed: Mar. 2, 2023

(65) Prior Publication Data

US 2023/0293131 A1    Sep. 21, 2023

Related U.S. Application Data

(60) Provisional application No. 63/269,407, filed on Mar. 16, 2022.

(51) Int. Cl.
| | |
|---|---|
| *A61B 6/50* | (2024.01) |
| *A61B 6/00* | (2024.01) |
| *A61B 6/42* | (2024.01) |
| *G06V 10/762* | (2022.01) |

(52) U.S. Cl.
CPC ............ *A61B 6/505* (2013.01); *A61B 6/4241* (2013.01); *A61B 6/5205* (2013.01); *G06V 10/762* (2022.01)

(58) Field of Classification Search
CPC ..... A61B 6/505; A61B 6/4241; A61B 6/5205; A61B 6/025; A61B 6/032; A61B 6/469; G06V 10/762; G06V 2201/03
See application file for complete search history.

(56) References Cited

U.S. PATENT DOCUMENTS

| | | | | |
|---|---|---|---|---|
| 2014/0064446 | A1* | 3/2014 | Wear | G01T 1/20185 |
| | | | | 250/366 |
| 2014/0105356 | A1* | 4/2014 | Yin | G01N 23/04 |
| | | | | 378/62 |
| 2018/0267177 | A1* | 9/2018 | Ishii | G01N 23/04 |
| 2018/0308233 | A1* | 10/2018 | Machida | A61B 6/505 |
| 2018/0325476 | A1* | 11/2018 | Machida | A61B 6/481 |
| 2019/0000409 | A1* | 1/2019 | Tamura | A61B 6/545 |
| 2019/0213715 | A1* | 7/2019 | Li | A61B 6/5258 |

(Continued)

OTHER PUBLICATIONS

Heymsfield, S. B. et al., "Multi-component molecular-level body composition reference methods: evolving concepts and future directions," Obes Rev. Apr. 2015: vol. 16, No. 4, pp. 282-294. DOI: 10.1111/obr.12261. Epub Feb. 3, 2015. PMID: 25645009; PMCID: PMC4464774.

(Continued)

*Primary Examiner* — David P Porta
*Assistant Examiner* — Gisselle M Gutierrez
(74) *Attorney, Agent, or Firm* — THE MARBURY LAW GROUP PLLC

(57) ABSTRACT

A method for determining bone mass density (BMD) of a patient includes obtaining X-ray scan data of a region of interest (ROI) of the patient using an energy discriminating photon counting radiation detector, and calculating the bone mass density (BMD) of the region of interest of the patient based on detected X-ray photon counts within three or more energy bins.

18 Claims, 8 Drawing Sheets

(56) References Cited

U.S. PATENT DOCUMENTS

| | | |
|---|---|---|
| 2020/0326290 A1 | 10/2020 | Iniewski et al. |
| 2020/0393576 A1 | 12/2020 | Harris et al. |
| 2021/0022695 A1 | 1/2021 | Iniewski et al. |
| 2021/0153823 A1* | 5/2021 | Schildkraut ............... A61B 6/51 |

OTHER PUBLICATIONS

Wear, J. et al., "CZT detector for dual-energy x-ray absorptiometry (DEXA)," Proc. SPIE 4142, Penetrating Radiation Systems and Applications II, (Dec. 18, 2000); https://doi.org/10.1117/12.410561.

* cited by examiner

SYSTEMS AND METHODS FOR MEASURING BONE MASS DENSITY USING ENERGY DISCRIMINATING PHOTON-COUNTING X-RAY DETECTOR

FIELD

The present disclosure relates generally to an X-ray detection systems and methods, and to more specifically to systems and methods for measuring bone mass density of a subject using an energy discriminating photon counting X-ray detector.

BACKGROUND

Osteoporosis is a skeletal disorder characterized by low bone mass and micro-architectural deterioration of bone tissue. Osteoporosis becomes more common with advanced age, and is particularly common among older women. It is estimated that one out of two Caucasian women over 50 years old will develop osteoporosis during their lifetime. Most of these cases are undiagnosed and untreated. This creates a significant public health concern due to the strong association between low bone mass and an increased risk of bone fractures. Within the elder population, fractures of the hips and legs due to falls result in significant healthcare costs and a substantial increase in mortality rate.

Diagnosis of osteoporosis and/or assessment of bone fracture risk is typically based on a measurement of Bone Mass Density (BMD), which is sometimes also referred to as Bone Mineral Density, of a patient. BMD is a measurement of the bone mineral content (BMC) of a patient within a particular region (e.g., arm, leg, etc.) or over the body, and is typically expressed in grams or kilograms per $cm^2$. The most widely used method for measuring BMD is Dual-Energy X-ray Absorptiometry (i.e., DEXA, or DXA). DEXA is an X-ray imaging technique that utilizes two X-ray beams at different energies directed at the body of a patient. A DEXA imaging scan typically uses a low radiation dose and provides relatively low image quality (e.g., ~0.4 line pairs/mm). A DEXA scan operates by measuring differences in the detected X-ray attenuation between the higher energy beam and the lower energy beam. Based on the measured differences in attenuation and the known variation in X-ray attenuation characteristics between bone and soft tissue at the different X-ray energies, the BMD of the patient may be estimated from the DEXA scan data.

Following the DEXA scan, patient diagnosis is typically based on a comparison of the BMD estimated from the DEXA scan to a reference index based on the average BMD of a young, healthy population and/or to the average BMD of individuals within the patient's peer group (e.g., based on age, sex, size, etc.). The comparison may be used to diagnose skeletal disorders such as osteopenia and osteoporosis, as well as for assessment of a patient's future risk of fractures.

A DEXA scan may also be used to provide an estimate of the body composition of a patient. In particular, concentrations of lipid and lean soft tissue can be estimated in areas of the patient containing only soft tissue. In areas of the patient containing both soft tissue and bone, the concentrations of lipids and/or lean soft tissue are typically extrapolated from surrounding regions of the patient that do not contain bone.

SUMMARY

Various embodiments include methods and systems for determining body mass composition, including bone mass density (BMD), using an X-ray imaging system having an energy discriminating photon counting radiation detector.

In one embodiment, a method for determining bone mass density (BMD) of a patient includes obtaining X-ray scan data of a region of interest (ROI) of the patient using an energy discriminating photon counting radiation detector, and calculating the bone mass density (BMD) of the region of interest of the patient based on detected X-ray photon counts within three or more energy bins.

In another embodiment, an X-ray system for determining bone mass density (BMD) of a patient comprises an X-ray source, an energy discriminating photon counting radiation detector having at least three energy bins, a patient support structure located between the X-ray source and the energy discriminating photon counting radiation detector, and a computing device configured to calculate the bone mass density (BMD) of a region of interest of the patient based on detected X-ray photon counts by the energy discriminating photon counting radiation detector within respective energy bins.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

Figure 1A:
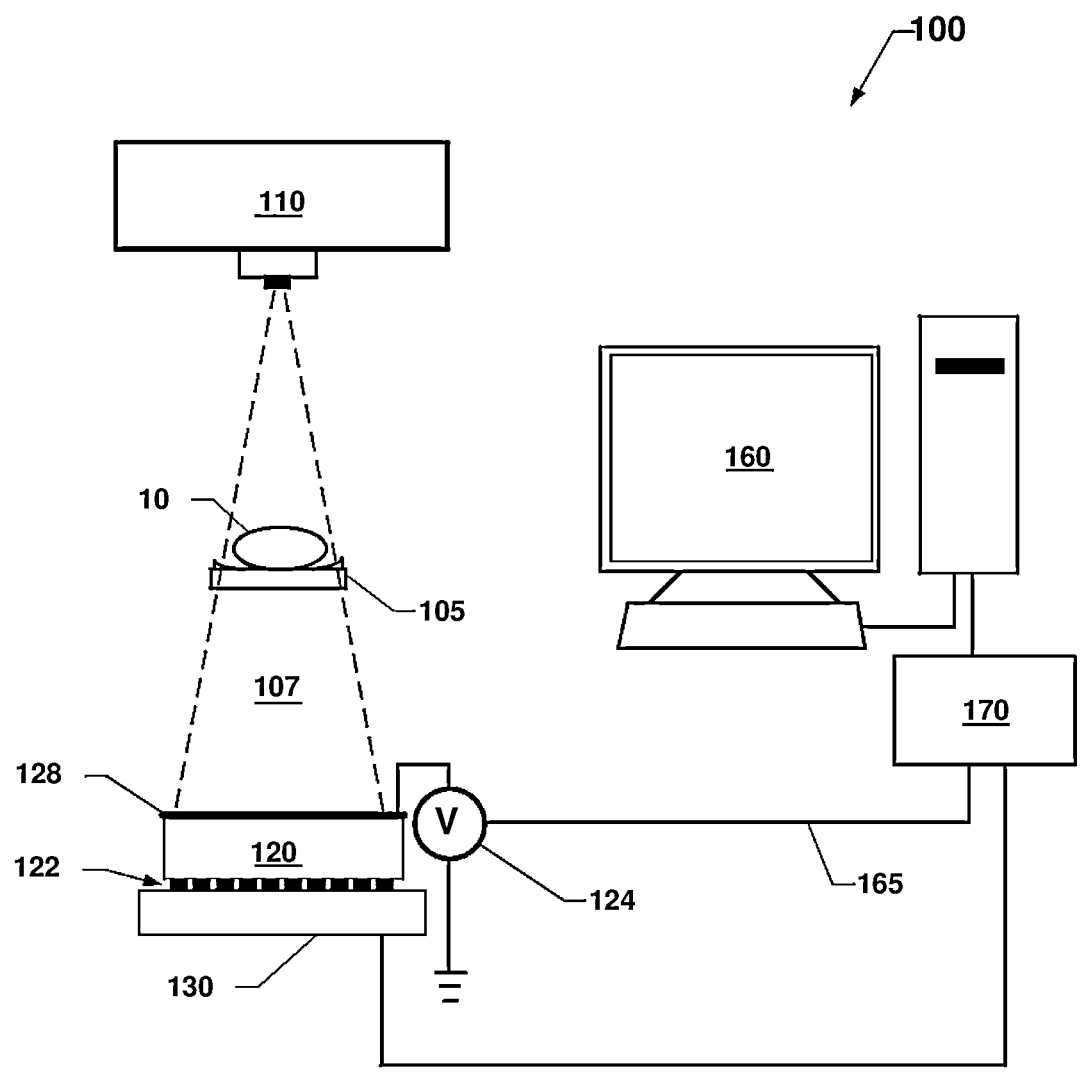
FIG. 1A is a block diagram of an X-ray imaging system suitable for use with various embodiments of the present disclosure.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims. Any reference to claim elements in the singular, for example, using the articles "a," "an," or "the" is not to be construed as limiting the element to the singular. The terms "example," "exemplary," or any term of the like are used herein to mean serving as an example, instance, or illustration. Any implementation described herein as an "example" is not necessarily to be construed as preferred or advantageous over another implementation. The drawings are not drawn to scale. Multiple instances of an element may be duplicated where a single instance of the element is illustrated, unless absence of duplication of elements is expressly described or clearly indicated otherwise.

Various embodiments are directed to measuring body composition of a patient, including bone mass density (BMD), fat composition and/or protein composition, using an X-ray imaging system having an energy discriminating photon counting X-ray radiation detector.

Despite its widespread use, the Dual-Energy X-ray Absorptiometry (i.e., DEXA) technique for measuring BMD suffers from number of fundamental problems which makes its application in clinical care problematic. For one, DEXA is a special X-ray imaging modality that is not typically available with general use X-ray systems because of the need for special beam filtering and near perfect spatial registration of two X-ray attenuation data sets. In particular, in order to produce a pair of X-ray beams having different effective energies, a DEXA system utilizes either a voltage switching or K-edge filtering scheme. In a voltage switching system, two X-ray tube voltage settings are used to create low and high X-ray energy beams. The X-ray tube power supply switches between a low voltage setting (for example 70 kVpp) and a high voltage setting (for example 140 kVpp) during alternate half cycles of the power supply. The resulting pulses are short (e.g., 8.33 ms for 60 Hz). Copper or brass is typically used to pre-harden the high energy beam, removing the low energy part of the spectrum and minimizing the overlap between low- and high-energy X-ray spectra. The filter, kVpp voltage switching, and X-ray detectors are all electronically and mechanically synchronized to sequentially collect information for each position of the X-ray gantry.

The other common technique for DEXA systems includes using a K-edge filter to split the X-ray output beam from the X-ray tube into low energy and high energy components. In the K-edge filter method, the X-ray tube may be operated in a steady direct current mode, and a K absorption edge filter located in the output path of the X-ray beam splits the energy spectrum of the beam into low and high energy components. The peak voltage (kVpp) of the tube is generally set so that the K-edge filter provides a notch or gap in the energy spectrum of the output beam. The K-edge filter typically includes one of several rare earth elements, such as samarium (K-edge=46.8 keV) or cerium (K-edge=40 keV).

In either of these cases, the DEXA system utilizes two effective X-ray energies and thus can only solve for two different materials simultaneously. Specifically, soft tissue composition can only be accurately estimated in areas of the patient that do not contain bone. In some cases, accurate estimates cannot be made in certain regions of the patient (e.g., head, hands, feet, and upper torso) that do not contain adequate soft tissue. Furthermore, in those pixels containing bone (which is typically 40% or more of the body image pixels), soft tissue composition must be estimated by extrapolating from neighboring pixels rather than directly measured. As a consequence, BMD measurements necessarily rely on certain assumptions regarding the composition of soft tissue surrounding the bone, which may not be accurate.

The simplifying assumptions made using DEXA can sometimes lead to unreliable measurements that may vary widely between different DEXA scanning devices and/or DEXA scanning devices made by different manufacturers. Errors between different DEXA scanners and/or attempts to convert measurements from one manufacturer's standard to another can introduce errors which can exceed the sensitivity of the BMD measurements, rendering the BMD measurements largely useless.

In addition, clinical interpretation and diagnoses based on DEXA measurements is based on a relative assessment rather than an absolute measurement. In other words, DEXA-based assessment of BMD relies on a comparison of the measured BMD against an imaginary average person having similar demographic characteristics, such as weight, height and ethnicity. However, an individual may have low BMD from birth and be erroneously assessed as having osteoporosis. In other cases, an osteoporotic individual who had an unusually high BMD from birth may be assessed as normal based on the DEXA test. This can lead to many instances of false positives and false negatives.

Another issue is that that the reference group to which the BMD test results are compared against may not be adequately representative of the patient or of the public at large. In many cases, the reference group may over represent certain demographic groups, such as Caucasian females, while underrepresenting other demographic groups, such as children, men, and/or individuals of some ethnic backgrounds, from which insufficient bone density data has been collected. This may skew the results of the BMD assessment, rendering them less reliable. In the case of children, special considerations must be taken into account in the use of DEXA scan data to assess bone mass in children. Specifically, comparing the bone mineral density of children to the reference data of adults will underestimate the BMD of children, because children have less bone mass than fully developed adults. This would lead to an over-diagnosis of osteopenia for children.

To address the above-described problems and provide a technique for providing absolute measure of bone mass density, various embodiments include systems and methods for measuring the body composition of a patient using an X-ray imaging system having an energy discriminating photon counting X-ray detector. An energy discriminating photon counting X-ray detector may operate by measuring currents induced in the detector by absorbed X-rays, and which are directly related to the energy of the absorbed X-rays. The measured current from each count is assigned to a particular range of energies, referred to as "bins" which correspond to a range of X-ray energies. The detector circuitry then counts the number of X-ray photon absorptions with measured currents that fall into each of the bins.

An energy discriminating photon counting X-ray detector according to various embodiments may include at least three energy bins, and preferably at least four energy bins (e.g., 4-6 energy bins). The multiple energy bins may be selected to enable measurement at least three, and preferably four or more, components of the human body, such as bone, fat, protein and water. The various embodiments provide an absolute bone mass density (BMD) measurement of all or a portion of a patient, such as a human patient.

An X-ray imaging system utilizing an energy discriminating photon counting X-ray detector in accordance with various embodiments may provide direct measurement at least three unknown body mass components, such as lipid (e.g., fat), lean soft tissue, and mineral (bone) components. In some embodiments, even greater accuracy may be achieved by directly measuring four or more body mass components, such as water, fat, protein, and mineral components, and potentially other residual body mass components such as glycogen, soft tissue minerals, and essential lipids. This is in contrast with conventional DEXA-based body mass composition measurements, which measure only two effective X-ray energies and thus require simplifying assumptions in order to solve for three or more unknown body mass components.

An X-ray imaging system for use in accordance with various embodiments may include an X-ray source and an energy discriminating photon counting X-ray detector. The X-ray source may be configured to direct a beam of X-ray radiation at a patient located between the X-ray source and the energy discriminating photon counting X-ray detector, where the X-ray photons which pass through the patient may be detected by the energy discriminating photon counting X-ray detector. The energy discriminating photon counting X-ray detector may detect counts of photons detected in each of a plurality of energy bins, such as at least three energy bins, including four or more energy bins (e.g., 4-6 energy bins), thereby providing measurements of the X-ray energy of the detected photons.

By utilizing methods and systems of the present embodiments, many of the fundamental problems of DEXA-based BMD and body composition measurement techniques may be resolved. In addition, since different energy levels of the X-ray radiation may be measured by the detector, a conventional X-ray source having a uniform energy profile of the output beam may be utilized, thus avoiding complicated and costly voltage switching and K-edge filtering schemes of conventional DEXA-based systems. In other words, in some embodiments, the X-ray source may operate at a single voltage to provide an X-ray beam having a constant (i.e., a single) energy beam during the entire scan of the patient. Furthermore, in some embodiments, the system may lack a K-edge filter such that the X-ray output beam from the X-ray source is not split into low energy and high energy components during the entire scan of the patient. Certain embodiments may also provide improved spatial resolution and precise assessment of body fat compositions.

FIG. 1A is a functional block diagram of an X-ray imaging system 100 in accordance with various embodiments. The X-ray imaging system 100 may include an X-ray source 110 (i.e., a source of ionizing radiation), and an energy discriminating photon counting radiation detector 120. The X-ray imaging system 100 may additionally include a patient support structure 105, such as a table or frame, which may rest on the floor and may support a biologic subject (i.e., a human or animal patient 10) to be scanned. The support structure 105 may be stationary (i.e., non-moving) or may be configured to move relative to other elements of the X-ray imaging system 100, such as the X-ray source.

The X-ray source 110 is typically mounted to a gantry and may move or remain stationary relative to the patient 10. The X-ray source 110 is configured to deliver ionizing radiation to the radiation detector 120 by emitting an X-ray beam 107 toward the patient 10 and the radiation detector 120. After the X-ray beam 107 is attenuated by the patient 10, the beam of radiation 107 is received by the radiation detector 120.

The radiation detector 120 may be controlled by a high voltage bias power supply 124 that selectively creates an electric field between an anode 122 and cathode 128 pair coupled thereto. In one embodiment, the radiation detector 120 includes a plurality of anodes 122 (e.g., one anode per pixel) and one common cathode 128 electrically connected to the power supply 124 and facing the X-ray source 110. The radiation detector 120 may include a detector material, such as a semiconductor material disposed between the anode 122 and cathode 128 and thus configured to be exposed to the electrical field therebetween. The semiconductor material may comprise any suitable semiconductor material for detecting X-ray radiation disposed between the anode 122 and cathode 128 and thus configured to be exposed to the electrical field therebetween. In various embodiments, the semiconductor material of the radiation detector 120 may comprise a II-VI semiconductor material, such as cadmium telluride, cadmium zinc telluride (i.e., CdZnTe or "CZT"), cadmium selenide telluride, and cadmium zinc selenide telluride. Other suitable semiconductor materials are within the contemplated scope of disclosure.

A read-out application specific integrated circuit (ASIC) 130 coupled to the anode(s) 122 may receive signals (e.g., charge or current) from the anode 122(s) and be configured to provide data to and by controlled by a control unit 170. The radiation detector 120 may be segmented or configured into a large number of small "pixel" detectors. In various embodiments, the pixel detectors of the radiation detector 120 and the ASIC 130 are configured to output data that includes counts of photons detected in each pixel detector in each of a number of energy bins. Thus, energy detectors 120 of various embodiments provide both two-dimensional detection information regarding where photons were detected, thereby providing image information, and measurements of the X-ray energy of the detected photons.

The control unit 170 may be configured to synchronize the X-ray source 110, the read-out ASIC 130, and the high voltage bias power supply 124. The control unit 170 may be coupled to and operated from a computing device 160. Alternatively, the computing device 160 and the control unit 170 may be integrated together as one device.

The patient 10 may slowly pass between the X-ray source 110 and the radiation detector 120 or alternatively the patient may remain stationary while the X-ray source 110 and the radiation detector 120 move relative to the patient 10. Either way, the radiation detector 120 may acquire X-ray attenuation data over a region of interest (ROI) of the patient 10.

The X-ray source 110 may include a collimator that may control the shape of the X-ray beam 107 that is emitted by the X-ray source 110. In some embodiments, the X-ray beam 107 may be a fan-shaped beam. Other beam shapes, such as a pencil-shaped beam or a cone-shaped beam, may also be utilized. The X-ray source 110 and detector 120 may move relative to the patient along one or more horizontal directions (e.g., along the x-axis direction and/or the z-axis direction i.e., into and out of the page in FIG. 1A) to scan across the patient 10 to obtain X-ray attenuation data over the ROI of the patient 10. The data acquired by the radiation detector 120 may be passed along to the computing device 160 that may be located remotely from the radiation detector 120 via a connection 165. The connection 165 may be any type of wired or wireless connection.

In one embodiment, the X-ray source 110 does not rotate about the long axis of the patient 10. Alternatively, or in addition, the X-ray source 110 and the radiation detector 120 may be configured to rotate completely or partially around the patient 10 to obtain incremental cross-sectional profiles of the patient 10 in a CT-type scan. If the connection 165 is a wired connection, the connection 165 may include a slip ring electrical connection between any structure (e.g., gantry) supporting the radiation detector 120 and a stationary support part of the support structure 105, which supports any part (e.g., a rotating ring). If the connection 165 is a wireless connection, the radiation detector 120 may contain any suitable wireless transceiver to communicate data with another wireless transceiver that is in communication with the computing device 160. The computing device 160 may include processing and imaging applications that analyze each profile obtained by the radiation detector 120, and a full set of profiles may be compiled to form a three-dimensional computed tomographic (CT) reconstruction of the patient 10 and/or two-dimensional images of cross-sectional slices of the patient 10.

Various alternatives to the design of the X-ray imaging system 100 of FIG. 1A may be employed to practice embodiments of the present disclosure. X-ray imaging systems may be designed in various architectures and configurations. For example, an X-ray imaging system may have a helical architecture. In a helical X-ray imaging scanner, the X-ray source 110 and radiation detector 120 are attached to a freely rotating gantry. During a scan, a table moves the patient 10 smoothly through the scanner, or alternatively, the X-ray source 110 and detector 120 may move along the length of the patient 10, creating helical path traced out by the X-ray beam. Slip rings may be used to transfer power and/or data on and off the rotating gantry. In other embodiments, the X-ray imaging system may be a tomosynthesis X-ray imaging system. In a tomosynthesis X-ray scanner, the gantry may move in a limited rotation angle (e.g., between 15 degrees and 60 degrees) in order to detect a cross-sectional slice of the patient 10. The tomosynthesis X-ray scanner may be able to acquire slices at different depths and with different thicknesses that may be reconstructed via image processing.

Figure 1B:
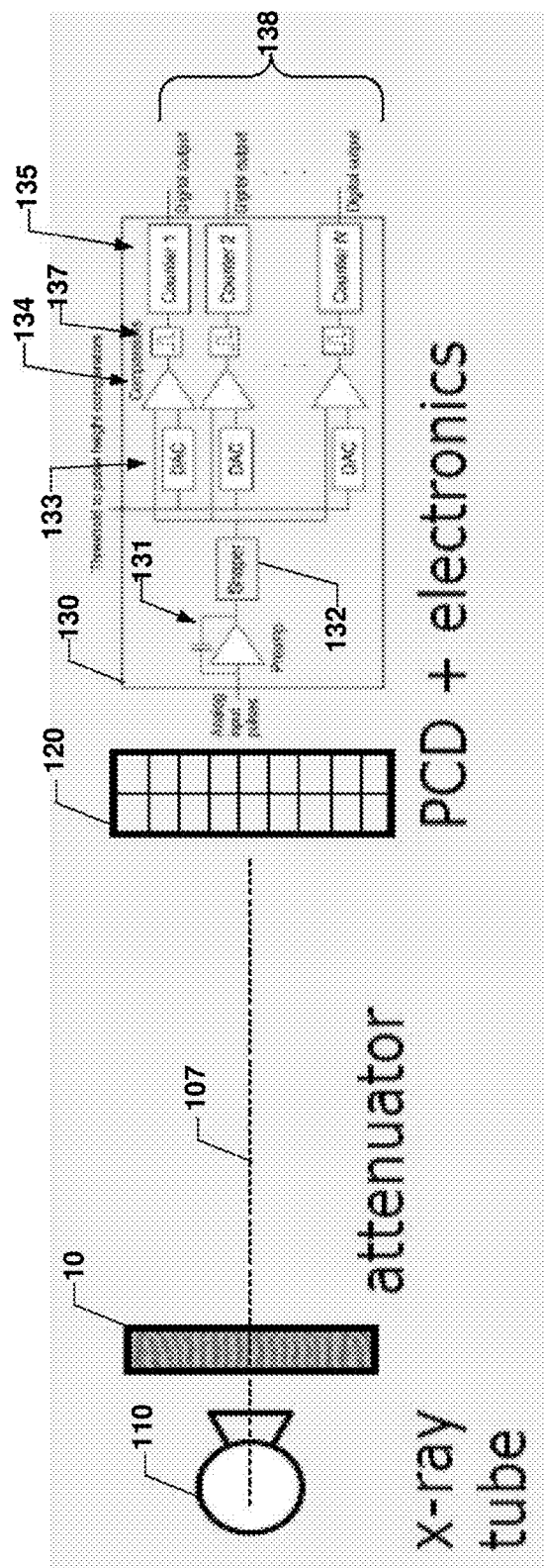
FIG. 1B is a block diagram illustrating components of an X-ray imaging system

FIG. 1B illustrates components of an X-ray imaging system, including components within the ASIC 130 configured to count X-ray photons detected in each pixel detector within a set of energy bins. As used herein, the terms "energy bin" and "bin" refer to a particular range of measured photon energies between a minimum energy threshold and a maximum energy threshold. For example, a first bin may refer to counts of photons determined to have an energy greater than a threshold energy (referred to as a trigger threshold, e.g., 20 keV) and less than 40 keV, while a second bin may refer to counts of photons determined to have an energy greater than 40 keV and less than 60 keV, and so forth.

X-rays 107 from an X-ray source (e.g., X-ray tube) 110 may be attenuated by a target (e.g., a patient 10) before interacting with the radiation detector material within the pixelated detector array 120. An X-ray photon interacting (e.g., via the photoelectric effect) with a pixelated radiation detector material generates an electron cloud within the material that is swept by an electric field to the anode electrode 122. The charge gathered on the anode creates a signal that is integrated by a charge sensitive amplifier (CSA) 131. There may be a CSA 131 for each pixel detector (e.g., for each anode 122) within the pixelated X-ray detector 120. The voltage of the CSA output signal may be proportional to the energy of the X-ray photon. The output signal of the CSA may be processed by an analog filter or shaper 132.

The filtered output may be connected to the inputs of a number of analog comparators 134, with each comparator connected to a digital-to-analog converter (DAC) 133 that inputs to the comparator a DAC output voltage that corresponds to the threshold level defining the limits of an energy bin. The detector circuitry 130 may be configured so that after the CSA voltage has stabilized (after the dead time), that voltage may be between two voltage thresholds set by two DACs 133, which determines the output of the comparators 134. Outputs from the comparators 134 may be processed through decision gates 137, with a positive output from a comparator 134 corresponding to a particular energy bin (defined by the DAC output voltages) resulting in a count added to an associated counter 135 for the particular energy bin. Periodically, the counts in each energy bin counter 135 are output as signals 138 to the control unit 170.

The detector array of an X-ray imaging system may include an array of radiation detector elements, referred to herein as pixel detectors. The signals from the pixel detectors may be processed by a pixel detector circuit, which may sort detected photons into energy bins based on the energy of each photon or the voltage generated by the received photon. When an X-ray photon is detected, its energy is determined and the X-ray photon count for its associated energy bin is incremented. For example, if the detected energy of an X-ray photon is 24 kilo-electron-volts (keV), the X-ray photon count for the energy bin of 20-40 keV may be incremented. The number of energy bins may be three or more, such as four to six. In an illustrative example, an X-ray photon counting detector may have four energy bins: a first bin for detecting photons having an energy between 20 keV and 40 keV, a second bin for detecting photons having an energy between 40 keV and 60 keV, a third bin for detecting photons having an energy between 60 keV and 90 keV, and a fourth bin for detecting photons having an energy above 90 keV (e.g., between 90 keV and 120 keV). The greater the total number of energy bins, the better the material discrimination.

Figure 2A:
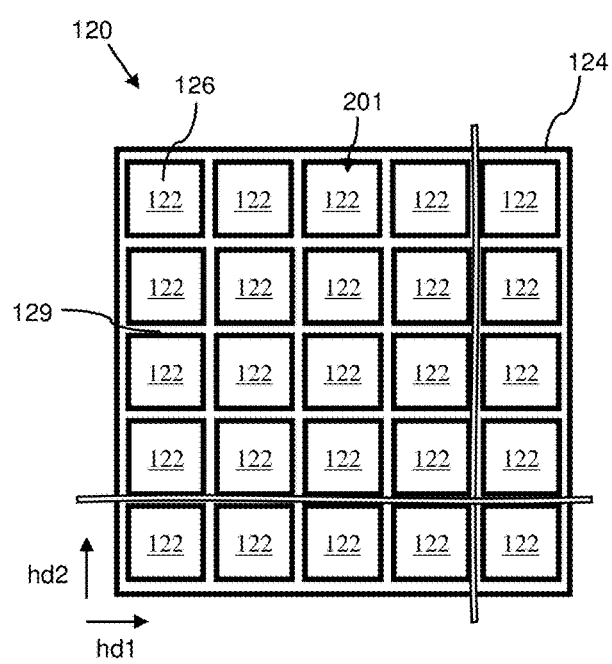
FIG. 2A illustrates a first side of a radiation detector for use with various embodiments of the present disclosure.
Figure 2B:
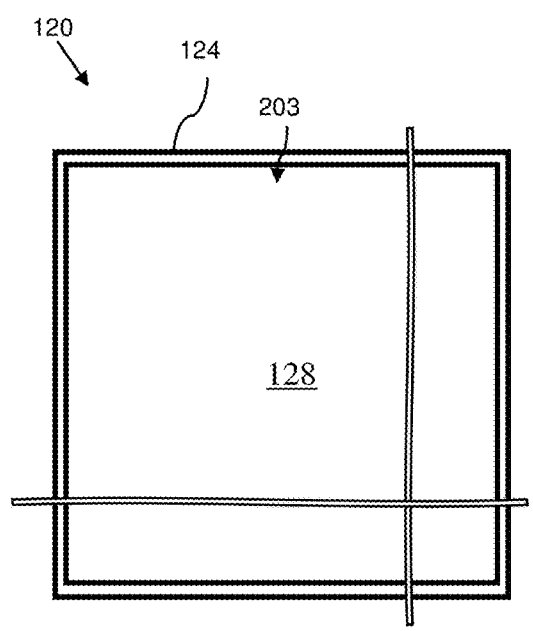
FIG. 2B illustrates a second side of the radiation detector of FIG. 2A.

FIGS. 2A-2B schematically illustrate a radiation detector, such as an energy discriminating photon counting radiation detector 120 for use in an X-ray imaging system 100 as shown in FIGS. 1A and 1B. FIG. 2A illustrates a first (e.g., anode) side 201 of the radiation detector 120, and FIG. 2B illustrates a second (e.g., cathode) side 203 of the radiation detector 120, opposite the first side 201. The radiation detector 120 includes a detector material, such as a semiconductor material substrate 124 (e.g., semiconductor wafer), such as a cadmium zinc telluride (CZT) substrate. Anode and cathode electrodes 122, 128 may be located over the semiconductor material substrate 124 on the first 201 and second 203 sides of the detector 120, respectively.

As shown in FIG. 2A, the first side 201 of the radiation detector 120 may include an array of discrete anode electrodes 122 comprised of an electrically conductive material, with gaps 129 between adjacent anode electrodes 122. Each anode electrode 122 may define a separate detector element (i.e., a pixel 126) of the radiation detector 120. As discussed above, a detector circuit, such as an application specific integrated circuit (ASIC) 130 shown in FIG. 1B, may be coupled to the anode electrodes 122 and may be configured to read out electric signals (e.g., charge or current) for each pixel 126 of the radiation detector 120. The gaps 129 between the adjacent anode electrodes 122 may also be referred to as "streets" or "roads." The "streets" 129 may be arranged in a regular grid pattern, as shown in FIG. 2A. Other geometries for the anode electrodes 122 and the streets 129 are within the contemplated scope of this disclosure, including anode electrodes 122 having non-uniform and/or non-rectangular shapes (e.g., triangular, elliptical and/or irregularly shaped anodes), as well as streets 129 having non-uniform spacing and/or widths.

Referring to FIG. 2B, the second side 203 of the radiation detector 120 may include a cathode electrode 128 comprised of an electrically conductive material. In the embodiment shown in FIG. 2B, the cathode electrode 128 may be a monolithic cathode electrode, meaning that a single cathode electrode 128 extends continuously over the surface of the semiconductor material substrate 124 located opposite to the first side 201 of the radiation detector 120. Alternately, the cathode electrode 128 may include a plurality of discrete segments of conductive material over the surface of the semiconductor material substrate 124, where each segment may correspond to a subset of one or more pixels 126 of the pixel array.

When an X-ray photon interacts with atoms of the semiconductor material 124 within the boundaries of a pixel 126 defined by an anode electrode 122, a cloud of electrons are ejected and gather on the anode electrode 122, where they are recorded as a count. The number of electrons (i.e., charge) collected on the anode 122 is reflective of the energy of the incoming photon, and thus a measurement of the energy of the detected photon can be determined from the charge or current detected on the anodes 122. An ASIC 130 coupled to each of the pixels 126 may be configured to count the X-ray photons detected in each pixel 126 within a set of energy bins, as described above with reference to FIG. 1B.

An X-ray imaging system 100 as described above may be used to determine body mass composition of a biological subject, including an absolute measurement of bone mass content (BMC) and/or bone mass density (BMD) (e.g., in units of weight per area) of a human or animal patient 10. The X-ray imaging system 100 may include an energy discriminating photon counting radiation detector 120 having at least three, and preferably four or more energy bins. A radiation detector 120 having at least four energy bins may enable precise discrimination of at least four components of the body, including water, lipids (e.g., fat), protein and mineral. In some embodiments, more than four energy bins may be used for discriminating five or more components of the body. Thus, unlike in DEXA systems as described above, no approximations or extrapolations are needed for assessing bone mass density. Further, in various embodiments, the X-ray source 110 may emit a single X-ray beam 107 having a uniform energy profile during a bone mass density scan without requiring a complicated voltage switching or K-edge filtering scheme, which may reduce the cost of the system 100 relative to conventional DEXA systems. In addition, the radiation detectors 120 according to various embodiments may have reduced pixel size compared to current DEXA systems (e.g., on the order of 1 mm or less), which may provide improved spatial resolution relative to DEXA systems. In addition to precise measurements of the BMD of a patient, various embodiments may also provide a precise measurement of body fat composition of the patient.

The energy bin thresholds of a radiation detector 120 according to various embodiments may encompass a continuous region of the energy spectrum between minimum and maximum photon energies that are detectable by the radiation detector 120. In one non-limiting example, the X-ray imaging system 100 may have a peak voltage of 120 kVpp, and the detectable energy range of the radiation detector 120 may be about 100 keV between a minimum detectable photon energy of ~20 keV (due to system noise) and a 120 keV maximum detectable photon energy without pile-up effect. In systems with a higher peak voltage, such as 140 kVpp, the detectable energy range may be larger (e.g., ~20 keV to ~140 keV).

Each energy bin may have an energy range that is sufficiently wide to ensure that a sufficient number of photons are collected within each bin. In one embodiment, each bin may cover an energy range of at least 20 keV. This enables at least four bins to cover the entire detectable energy range of the radiation detector 120. In some embodiments, up to five or six energy bins may be utilized. The threshold energies for the bins may be set to roughly equalize the photon counts for each of the bins.

In one non-limiting example, the radiation detector may 120 include four energy bins, which may be denoted as $Bin_0$ through $Bin_3$. The ranges of the bins may be as follows: $Bin_0$=20 to 40 keV (e.g., ≥20 keV and <40 keV), $Bin_1$=40 to 60 keV (e.g., ≥40 keV and <60 keV), $Bin_2$=60 to 90 keV (e.g., ≥60 keV and <90 keV), and $Bin_3$=90 to 120 keV (e.g., ≥90 keV and ≤120 keV). Other suitable threshold energies for the energy bins may be utilized in various embodiments.

Figure 3A:
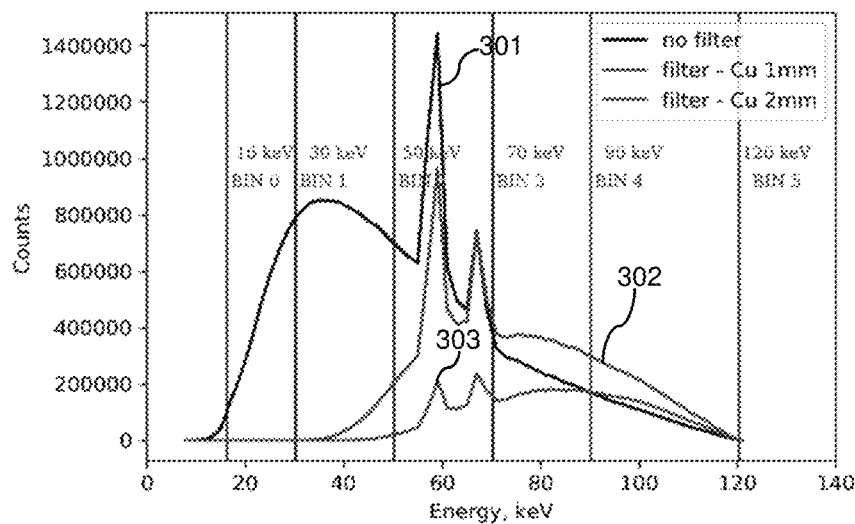
FIGS. 3A and 3B are plots showing total detected photon count distribution (FIG. 3A) and a normalized detected photon count distribution (FIG. 3B) over simulated X-ray energy spectra overlaid with the locations of energy bins of an energy discriminating photon counting radiation detector according to an embodiment of the present disclosure.
Figure 3B:
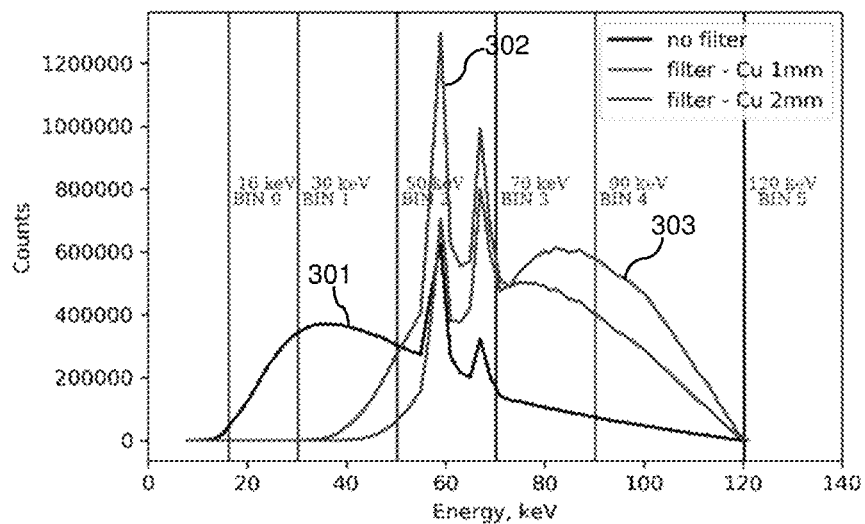

FIGS. 3A and 3B are plots showing detected photon counts over simulated X-ray energy spectra overlaid with the locations of energy bins of an energy discriminating photon counting radiation detector 120 according to an embodiment of the present disclosure. In the example of FIGS. 3A and 3B, the radiation detector 120 includes six (6) energy bins. $Bin_0$ extends between 16 and 30 keV (e.g., ≥16 keV and <30 keV), $Bin_1$ extends between 30 and 50 keV (e.g., ≥30 keV and <50 keV), $Bin_2$ extends between 50 and 70 keV (e.g., ≥50 keV and <70 keV), $Bin_3$ extends between 70 and 90 keV (e.g., ≥70 keV and <90 keV), $Bin_4$ extends between 90 and 120 keV (e.g., ≥90 keV and <120 keV), and $Bin_5$ includes photon energies of 120 keV or more (e.g., ≥120 keV). FIG. 3A illustrates the total photon count distribution and FIG. 3B illustrates the photon count distribution normalized to represent the same number of photons in each energy spectrum. The plots illustrated in FIGS. 3A and 3B include photon counts from a 120 kVpp incident X-ray beam with no filter (line 301), a 120 kVpp incident X-ray beam with a 1 mm thick copper (Cu) filter between the X-ray source and detector (line 302), and a 120 kVpp incident X-ray beam with a 2 mm thick Cu filter between the X-ray source and detector (line 303). The three different X-ray energy spectra illustrated in lines 301, 302 and 303 approximate the differences in the attenuation of the X-ray radiation at different energy levels when passing through components of the body having different X-ray absorption characteristics.

As shown in FIGS. 3A and 3B, in the case when no filter is used (line 301) the highest total photon counts are in $Bin_1$ and $Bin_2$. With a 1 mm Cu filter (line 302), the highest photon counts are in $Bin_2$ and $Bin_3$. With a 2 mm Cu filter (line 303), the highest photon count is in $Bin_3$, followed by $Bin_4$ and $Bin_2$. The divisions of counts between the respective energy bins depends on the number of energy thresholds and their positions on the photon energy spectrum, the peak voltage (kVpp) of the X-ray tube, the material(s) through which the X-ray beam passes before reaching the detector, and the relative thickness(es) of the material(s) through which the X-ray beam passes. For bone densitometry testing, various parameters such as the number and location(s) of the energy thresholds and the peak voltage of the X-ray tube may be configured to optimize the extraction of bone density information from the scan data.

A method for determining BMD of a patient using an X-ray imaging system having an energy discriminating photon counting radiation detector according to one embodiment will now be described. Within the X-ray diagnostic energy range, the two dominating X-ray interaction effects are photo-electric effect (PE) and Compton scattering (CS). Both are typically assumed to be smoothly varying functions with separable and independent material and energy dependences. Most elements appearing naturally in the human body have low atomic number and therefore lack absorption edges in the X-ray energy range used for medical imaging. Therefore, in some embodiments, the method may neglect K-edge effects.

The energy discriminating photon counting detector measures the counts in the pre-defined energy bins as discussed above. The measured counts may be converted to attenuation coefficients μ for the respective energy bins using standard photon-counting calibration techniques that utilize various radiation sources and phantoms.

There are a number of human body composition models described in the literature. A common and sufficiency accurate model for the purpose of the Bone Density measurements is 4-components model that assumes the body consists of water, bone, fat and protein. The linear attenuation coefficient μ can be expanded to account these four components as a linear combination:

$$\mu = \mu_{water} + \mu_{bone} + \mu_{fat} + \mu_{protein} \quad \text{[Eq. 1]}$$

Each linear attenuation coefficient $\mu_i$ (where "i" is either water, bone, fat or protein) contains both a photo-electric component $f_{PE}$ and a Compton scattering component $f_{CS}$. The photo-electric component of the attenuation coefficient is assumed to be proportional to mass density and depends strongly on atomic number Z (which is proportional to product of density ϱ and $Z^3$), whereas the Compton scattering component of the attenuation coefficient can be described by its density dependence alone ($\alpha_{CS}$ is proportional to the density ϱ). The photo-electric effect has cubic dependence on photon energy E (and is inversely proportional to $E^3$). On the other hand, the Compton-scattering energy dependence is relatively flat over the diagnostic energy range and is often modelled by the Klein-Nishina cross section. As a result, all four of the attenuation coefficients (for water, bone, fat and protein) may be represented as follows:

$$\mu_i = \alpha_{PE} * f_{PEi} + \alpha_{CS} * f_{CSi} \quad \text{[Eq. 2]}$$

where the component $\alpha_{PE}$ is a fraction of the photo-electric events and $\alpha_{CS}$ is a fraction of the Compton scatter events. There are various ways to model photo-electric effect and Compton scatter reported in the literature. As a result, there are various ways to solve the set of equations given by Equations 1 and 2. In particular, photon counts from four energy bins are sufficient to solve for the four unknown human body constituents of water, bone, fat and protein. This is in contrast to a standard DEXA system that utilizes two X-ray energy values (low and high energy) which can only solve for two body constituents (e.g., water and bone), or extrapolated (with limited accuracy) to three body constituents (e.g., water, bone, fat) when certain approximating assumptions are made.

Figure 4:
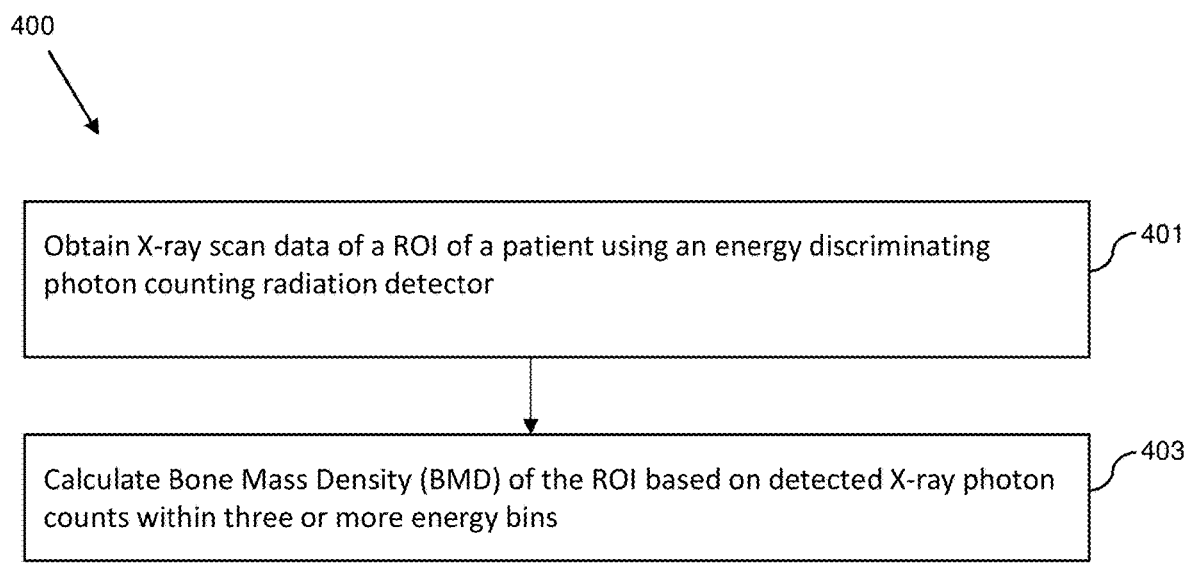
FIG. 4 is a flow diagram illustrating a method for determining bone mass density (BMD) of a patient according to an embodiment of the present disclosure.

FIG. 4 is a flow diagram illustrating a method 400 for determining bone mass density (BMD) of a patient. The method 400 of FIG. 4 may be implemented using an X-ray imaging system 100 having an energy discriminating photon counting radiation detector 120 such as shown and described above with reference to FIGS. 1A-2B. The ASIC 130 is configured to output data that includes counts of photons detected in each pixel of the detector 120 in each of three or more energy bins. In block 401 of embodiment method 400, X-ray scan data of a region of interest (ROI) of a patient 10 may be obtained using an energy discriminating photon counting radiation detector 120. The region of interest (ROI) may include all or a portion of the lumbar spine, the proximal hip, the distal forearm, or any other suitable location on the body of the patient 10. In some embodiments, the ROI may encompass the entire body of the patient (e.g., for a full-body scan).

The scan data may be obtained by directing a beam of X-ray radiation from the X-ray source 110 at the ROI of the patient 10 such that X-ray photons which pass through the patient may be detected by the energy discriminating photon counting X-ray detector 120. The beam of X-ray radiation may have any suitable geometry (e.g., pencil-beam, fan-beam, cone-beam, etc.). The X-ray source 110 and the detector 120 and patient 10 may be moved relative to each other (e.g., the X-ray source 110 and the detector 120 may be translated and/or rotated relative to the patient 10) in order to scan over the entire ROI of the patient 10. In embodiments, during the entire scan, the X-ray tube of the X-ray source 110 may operate at a single peak voltage (kVpp) to provide an output X-ray beam having a uniform energy profile (i.e., no voltage switching). In various embodiments, there may be no K-edge filter disposed between the X-ray tube and the patient 10. The detector 120 may register the counts of X-ray photons impinging on the detector 120 within each of the three or more energy bins.

The energy bins may encompass a continuous region of the energy spectrum between minimum and maximum photon energies that are detectable by the radiation detector 120. The energy thresholds of the energy bins may be configured to detect for a different body mass constituent of the patient 10, such as for example, bone, lipid and lean soft tissue. As used herein, an energy bin may be configured to detect for a particular body mass constituent where the particular constituent has a measurable difference in its X-ray absorption coefficient relative to at least one other body mass constituent within the energy range encompassed by the energy bin. In some embodiments, the energy discriminating photon counting radiation detector 120 output may be provided by the ASIC 130 into at least four energy bins (e.g., 4-6 energy bins), and the energy bins may be configured to detect for at least four body mass constituents of the patient, such as bone, water, fat and protein.

In step 403 of method 400, the bone mass density (BMD) of the region of interest (ROI) of the patient 10 may be calculated based on the detected X-ray photon counts within the respective energy bins. As discussed above, the detected photon counts in the respective energy bins may be used to solve for at least three body constituents, including bone (mineral) content. For example, with four or more energy bins, the detected photon counts in each bin may be used to solve for at least four body constituents, such as bone, water, fat, and protein. Based on the relative compositions of the at least three body constituents, an absolute measurement of the bone mass density (BMD) of the region of interest (ROI) may be determined.

Figure 5:
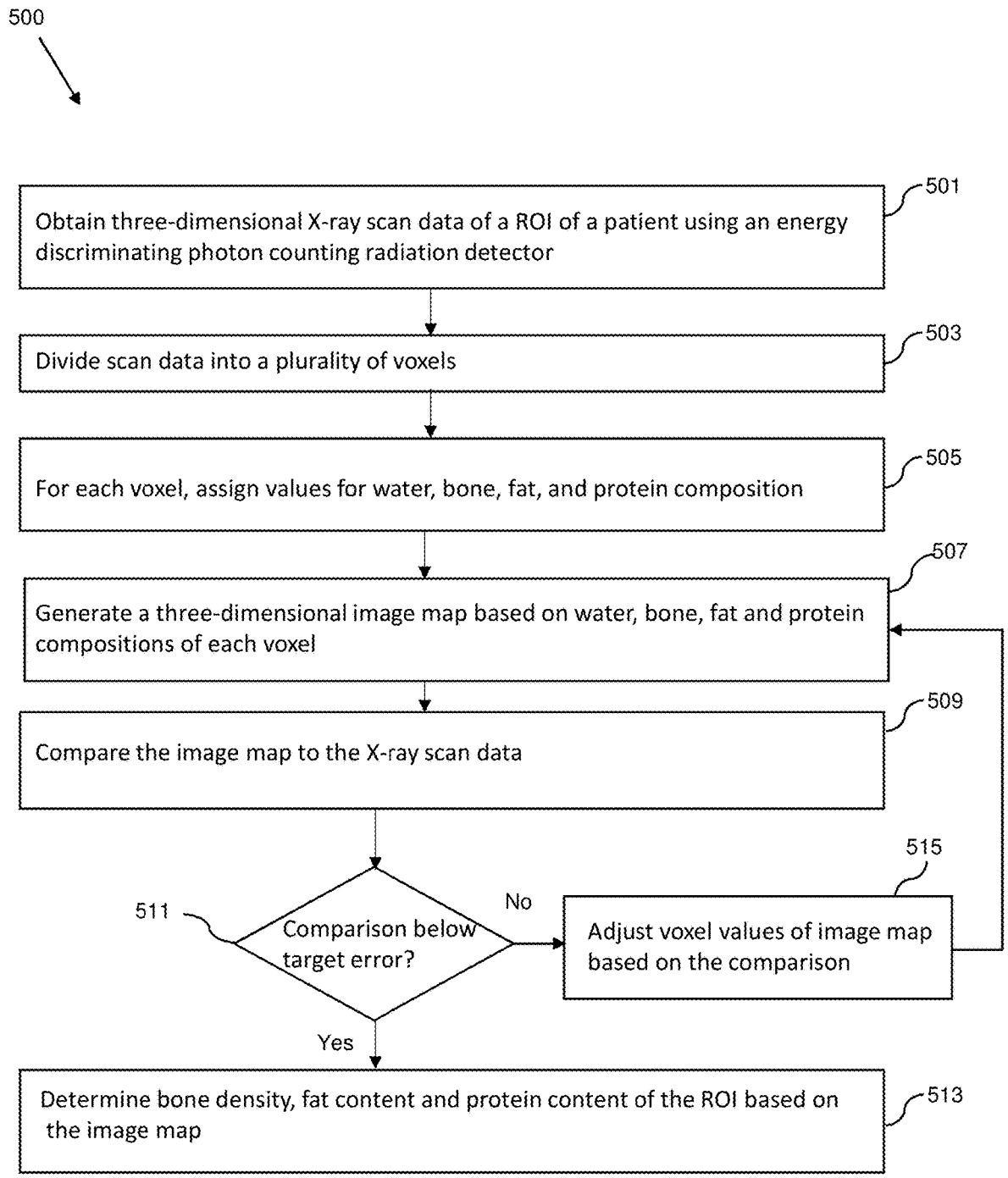
FIG. 5 is a flow diagram illustrating a method for determining bone mass density (BMD), fat and protein content of a region of interest (ROI) of a patient according to an embodiment of the present disclosure.

FIG. 5 is a flow diagram illustrating a method 500 for determining bone mass density (BMD), fat and protein content of a region of interest (ROI) of a patient 10. The method 500 of FIG. 5 may be implemented using an X-ray imaging system 100 having an energy discriminating photon counting radiation detector 120 as shown and described above with reference to FIGS. 1A-2B. In block 501 of embodiment method 500, three-dimensional X-ray scan data of a region of interest (ROI) of a patient 10 may be obtained using an energy discriminating photon counting radiation detector 120. In various embodiments, during the X-ray imaging scan, the X-ray source 110 and the detector 120 combination and the patient 10 may move relative to each other while the detector 120 and the ASIC 130 may register the counts of X-ray photons impinging on the detector 120 within each of a plurality of energy bins. In various embodiments, the X-ray source 110 may direct a fan- or cone-shaped beam of X-ray radiation at the patient 10. The detector 120 may include a two-dimensional array of pixel elements that may register counts of incident X-ray photons within the respective energy bins at each pixel location during the scan. The computing device 160 coupled to the detector 120 may include processing and imaging applications that are configured to analyze the scan data obtained by the radiation detector 120 and the ASIC 130. In some embodiments, the X-ray source 110 and the detector 120 may obtain scan data of the patient over multiple projection angles, such as by rotating around the patient axis, and the computing device 160 may be configured to generate a three-dimensional reconstructed image of the ROI of the patient 10. In some embodiments, the X-ray source 110 and the detector 120 may be moved along the length of the patient 10 to obtain scan data at multiple viewing angles with respect to the patient 10 (e.g., top and side views of the patient 10), and the resulting scan data may be used to reconstruct a quasi-3D image of the ROI. The three-dimensional or quasi-3D reconstructed image of the ROI may provide a higher spatial resolution than is achievable using a conventional DEXA scanning device. In one non-limiting example, a three-dimensional reconstructed image may enable identification of features of less than 1 mm in size, including less than 0.5 mm (e.g., 350 µm or less).

Figure 6A:
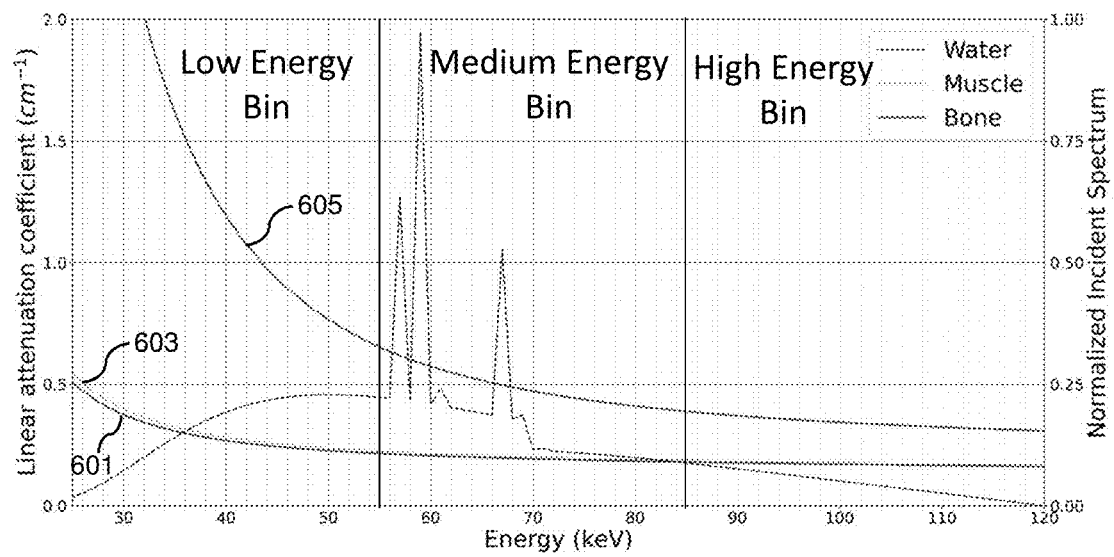
FIG. 6A is a plot illustrating the linear attenuation coefficients for three body constituent components-water, muscle, and bone-over the X-ray energy spectrum between 25 keV and 120 keV.
Figure 6B:
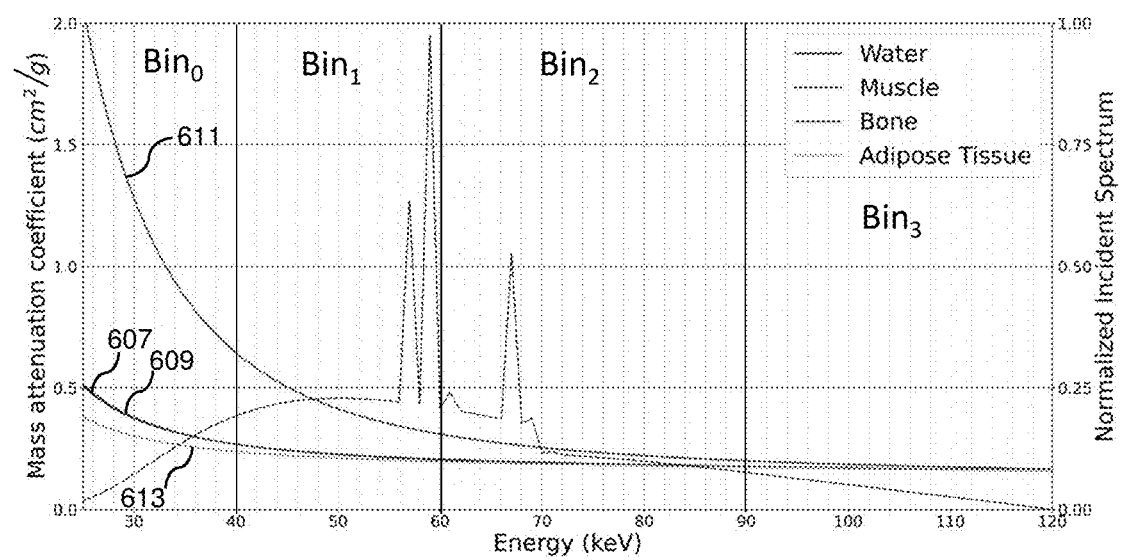
FIG. 6B is a plot illustrating the mass attenuation coefficients for four body constituent components-water, muscle, bone, and adipose tissue-over the X-ray energy spectrum between 25 keV and 120 keV.

In step 503 of embodiment method 500, the scan data may be divided into a plurality of voxels. Each voxel may represent a three-dimensional sub-volume of the ROI of the patient 10. In step 505 of embodiment method 500, each voxel may be assigned values for water, bone, fat, and protein composition. Various components in the human body attenuate the X-ray signal in different ways as a function of the X-ray photon energy. FIG. 6A is a plot illustrating the linear attenuation coefficients ($cm^{-1}$) for three body constituent components, water 601, muscle 603, and bone 605, over the X-ray energy spectrum between 25 keV and 120 keV. FIG. 6B is a plot illustrating the mass attenuation coefficients ($cm^2/g$) for four body constituent components, water 607, muscle 609, bone 611, and adipose tissue 613 (i.e., fat), over the X-ray energy spectrum between 25 keV and 120 keV. The dotted lines in FIGS. 6A and 6B illustrate the normalized incident x-ray energy spectrum. A spectral photon counting detector is able to exploit these differences in X-ray attenuation properties in a manner that an energy integrated detector is not able to. For example, the ratios of photon counts in different energy bins (e.g., Low, Medium and High Energy $Bin_5$ as shown in FIG. 6A, or $Bin_0$-$Bin_3$ in FIG. 6B) may be used to make an initial assessment of the body composition of each voxel. Various combinations of energy bins may be used to fine tune the initial assessment algorithm (high to medium, high to low, medium to low, etc.) with an increased number of components (e.g., protein) and number of energy bins (e.g., extending from 3 to 4 and beyond, etc.).

In step 507 of embodiment method 500, a three-dimensional image map of the ROI may be generated based on the assigned values of water, bone, fat and protein composition of the respective voxels. The three-dimensional image map may be generated based on the known X-ray absorption coefficients of water, bone, fat and protein, and the relative concentrations of each of these body constituents based on the assigned values of water, bone, fat and protein composition within the respective voxels.

In step 509 of embodiment method 500, the three-dimensional image map generated in step 507 may be compared to the three-dimensional X-ray scan data obtained in step 501. The comparison may include identifying a difference between the measured three-dimensional X-ray scan data and the generated three-dimensional image map. In various embodiments, the comparison may include comparing radiodensity/greyscale values of each voxel from the measured image to the corresponding voxels of a simulated image based on the assigned values of water, bone, fat and protein composition for each voxel. In determination block 511 of embodiment method 500, a determination may be made as to whether a difference between the measured three-dimensional X-ray scan data and the generated three-dimensional image map is below a target error value. The target error value may be determined in a number of ways. For example, the root mean square (RMS) error may be calculated for every voxel as the difference between computed and measured values, and the target error value may be a predetermined minimum RMS error value. In other embodiments, the total error may be assessed using machine learning and/or artificial intelligence (AI) algorithms. In response to a determination that a difference between the measured three-dimensional X-ray scan data and the generated three-dimensional image map is below a target error value (i.e., determination block 511="Yes"), the method 500 may proceed to step 513. In step 513, the bone density, fat content and the protein content of the ROI of the patient 10 may be determined based on the generated three-dimensional image map.

In response to a determination that a difference between the measured three-dimensional X-ray scan data and the generated three-dimensional image map is not below a target error value (i.e., determination block 511="No"), the method 500 may proceed to step 515. In step 515, the values of water, bone, fat and protein composition in one or more voxels may be adjusted, and the method may return to step 509 to generate an updated three-dimensional image map based on the adjusted values of water, bone, fat and protein composition. This process may repeat iteratively until the difference between the measured three-dimensional X-ray scan data and the generated three-dimensional image map is below the target error value (i.e., determination block 511="Yes"). The method 500 may then proceed to step 513 where the bone density, fat content and the protein content of the ROI of the patient 10 may be determined based on the current iteration of the three-dimensional image map.

The process of iteratively adjusting the water, bone, fat and protein of the voxels may be performed using a clustering K-means algorithm in various embodiments. K-means clustering is a method of vector quantization, originally from signal processing, that aims to partition n observations into K clusters (the clusters being different body constituents, such as water, bone, fat, and protein) in which each observation belongs to the cluster with the nearest mean (cluster centers or cluster centroid), serving as a prototype of the cluster. This results in a partitioning of the data space (measured counts map containing energy information) into so called Voronoi cells. K-means clustering minimizes within-cluster variances (squared Euclidean distances): the mean optimizes squared errors. The problem is computationally difficult (NP-hard); however, efficient heuristic algorithms converge quickly to a local optimum, each OEM can develop its own heuristic. These are usually similar to the expectation-maximization algorithm for mixtures of Gaussian distributions via an iterative refinement approach employed by both K-means and Gaussian mixture modeling. They both use cluster centers to model the data; however, K-means clustering tends to find clusters of comparable spatial extent, while the Gaussian mixture model allows clusters to have different shapes.

Figure 7:
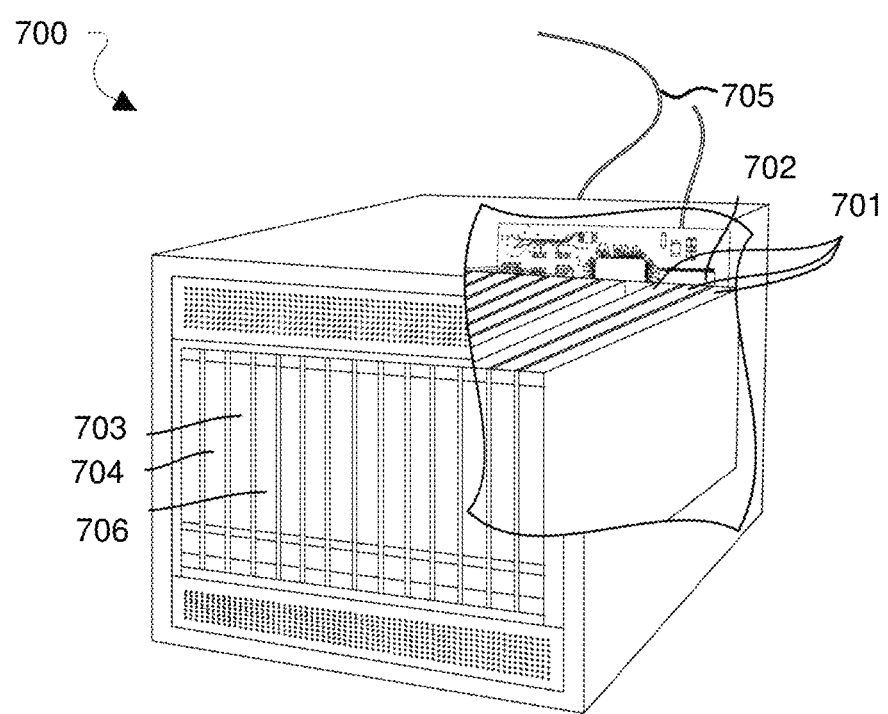
FIG. 7 is a component block diagram illustrating an example computing system suitable for use with the various embodiments.

Various embodiments (including, but not limited to, the embodiment methods described above with reference to FIGS. 4 and 5) may be implemented in computing systems, such as any of a variety of commercially available computers 700 as illustrated in FIG. 7. Such a computer 700 typically includes one or more processors 701 coupled to volatile memory 702 and a large capacity nonvolatile memory, such as a disk drive 704. As illustrated in FIG. 7, one or more processors 701 may be added to the computer 700 by inserting them into the racks of the assembly. The computer 700 may also include a floppy disc drive, compact disc (CD) or digital versatile disc (DVD) disc drive 706 coupled to the one or more processors 701. The computer 700 may also include network access ports 703 coupled to the one or more processors 701 for establishing network interface connections with a network 705, such as a local area network coupled to other computers and servers, or the Internet.

The present embodiments may be implemented in systems used for medical imaging, such as X-ray imaging, as well as for non-medical imaging applications, such as industrial inspection applications.

Computer program code or executable instructions for execution on a programmable processor for carrying out operations of the various embodiments may be written in a high level programming language such as C, C++, C#, Smalltalk, Java, JavaScript, Visual Basic, a Structured Query Language (e.g., Transact-SQL), Perl, or in various other programming languages. Embodiments may be implemented as program code or processor-executable instructions stored on a non-transitory processor-readable storage medium that are configured to cause a processor coupled to a pixelated radiation detector, such as a processor or analysis unit of an X-ray imaging system, to perform operations of any of the various embodiments. Program code or processor-executable instructions stored on a non-transitory processor readable storage medium as used in this application may refer to machine language code (such as object code) whose format is understandable by a processor. Non-transitory processor-readable storage medium include any form of media used for storing program code or processor-executable instructions including, for example, RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a processor or computer.

While the disclosure has been described in terms of specific embodiments, it is evident in view of the foregoing description that numerous alternatives, modifications and variations will be apparent to those skilled in the art. Each of the embodiments described herein may be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:

1. A method for determining bone mass density (BMD) of a patient, comprising:
    obtaining three-dimensional X-ray scan data of a region of interest (ROI) of the patient using an energy discriminating photon counting radiation detector;
    calculating the bone mass density (BMD) of the region of interest of the patient based on detected X-ray photon counts within three or more energy bins;
    dividing the three-dimensional scan data into a plurality of voxels;
    assigning values corresponding to water, bone, fat and protein composition to each voxel of the plurality of voxels;
    generating a three-dimensional image map based on the assigned values corresponding to water, bone, fat and protein composition of each voxel of the plurality of voxels;
    comparing the generated three-dimensional image map to the three-dimensional X-ray scan data; and
    determining the bone density, fat content and protein content of the ROI of the patient in response to a determination that a difference between the three-dimensional image map and the three-dimensional X-ray scan data is below a threshold error value.

2. The method of claim 1, wherein obtaining the three-dimensional X-ray scan data comprises directing a beam of X-ray radiation from an X-ray source at the ROI of the patient such that X-ray photons that pass through the ROI of the patient are detected by the energy discriminating photon counting radiation detector.

3. The method of claim 2, wherein an X-ray tube of the X-ray source operates at a single peak voltage to provide an output beam having a uniform energy profile while the three-dimensional X-ray scan data is obtained.

4. The method of claim 3, wherein the X-ray beam is directed from the X-ray source to the ROI of the patient without passing through a K-edge filter.

5. The method of claim 2, wherein the energy bins of the energy discriminating photon counting X-ray detector encompasses a continuous region of the energy spectrum of the X-ray beam between minimum and maximum photon energies that are detectable by the radiation detector.

6. The method of claim 2, wherein obtaining the three-dimensional X-ray scan data comprises moving the X-ray source and the energy discriminating photon counting X-ray detector relative to the patient to scan over the entire ROI of the patient.

7. The method of claim 6, wherein the ROI of the patient comprises at least one of the lumbar spine, the proximal hip and the distal forearm of the patient.

8. The method of claim 1, wherein calculating the bone mass density (BMD) of the ROI of the patient comprises calculating an absolute measurement of the BMD of the ROI of the patient in units of weight per area.

9. The method of claim 1, wherein:
    the energy discriminating photon counting X-ray detector comprises a II-VI semiconductor material located between at least one cathode electrode and a plurality of anode electrodes; and
    each of the plurality of anode electrodes defines a separate pixel of the detector.

10. The method of claim 9, wherein the energy discriminating photon counting radiation detector further comprises a read-out circuit coupled to the plurality of anode electrodes and configured to output data that includes counts of photons detected in each pixel in each of the at least three energy bins.

11. The method of claim 1, wherein energy thresholds of each energy bin of the at least three energy bins are configured to detect for a different body mass constituent of the patient.

12. The method of claim 11, wherein the different body mass constituents comprise bone, lipid and lean soft tissue of the patient.

13. The method of claim 11, wherein the energy discriminating photon counting radiation detector comprises at least four energy bins.

14. The method of claim 13, wherein the energy thresholds of each energy bin of the at least four energy bins are configured to detect for different body mass constituents comprising water, bone, fat and protein.

15. The method of claim 1, wherein values corresponding to water, bone, fat and protein composition are assigned to each voxel based on ratios of photon counts detected in different energy bins.

16. The method of claim 1, further comprising:
adjusting the values corresponding to water, bone, fat and protein content in one or more voxels in response to a determination that the difference between the three-dimensional image map and the three-dimensional X-ray scan data is not below the threshold error value;
generating an updated three-dimensional image map based on the adjusted values corresponding to water, bone, fat and protein content in one or more voxels; and
comparing the updated three-dimensional image map to the three-dimensional X-ray scan data; and
determining the bone density, fat content and protein content of the ROI of the patient in response to a determination that a difference between the updated three-dimensional image map and the three-dimensional X-ray scan data is below the threshold error value.

17. The method of claim 16, wherein the steps of adjusting the values corresponding to water, bone, fat and protein content in one or more voxels, generating an updated three-dimensional image map based on the adjusted values, and comparing the updated three-dimensional image map to the three-dimensional X-ray scan data are repeated until the difference between the updated three-dimensional image map and the three-dimensional X-ray scan data is determined to be below the threshold error value.

18. The method of claim 17, wherein the values corresponding to water, bone, fat and protein in the one or more voxels are adjusted using a K-means clustering algorithm.

* * * * *